US012766276B2

(12) United States Patent
Helmlinger et al.

(10) Patent No.: US 12,766,276 B2
(45) Date of Patent: Oct. 20, 2026

(54) DISPENSER AND ANALYSIS UNIT FOR SAME

(71) Applicant: Aptar Radolfzell GmbH, Radolfzell (DE)

(72) Inventors: Michael Helmlinger, Radolfzell-Böhringen (DE); Jörg Kohnle, Villingen-Schwenningen (DE)

(73) Assignee: Aptar Radolfzell GmbH, Radolfzell (DE)

(*) Notice: Subject to any disclaimer, the term of this patent is extended or adjusted under 35 U.S.C. 154(b) by 81 days.

(21) Appl. No.: 18/859,783

(22) PCT Filed: Apr. 6, 2023

(86) PCT No.: PCT/EP2023/059209
§ 371 (c)(1),
(2) Date: Oct. 24, 2024

(87) PCT Pub. No.: WO2023/208568
PCT Pub. Date: Nov. 2, 2023

(65) Prior Publication Data

US 2025/0269122 A1 Aug. 28, 2025

(30) Foreign Application Priority Data

Apr. 26, 2022 (EP) .................................... 22170085

(51) Int. Cl.
*A61M 15/00* (2006.01)
*A45D 40/26* (2006.01)
(Continued)

(52) U.S. Cl.
CPC ........... *A61M 15/008* (2014.02); *A45D 40/26* (2013.01); *A61J 1/05* (2013.01); *A61M 11/008* (2014.02);
(Continued)

(58) Field of Classification Search
CPC .. A61M 15/008; A61M 11/008; A61M 15/08; A61M 2205/332;
(Continued)

(56) References Cited

U.S. PATENT DOCUMENTS 3,584,348 A 6/1971 Soltysik
4,325,503 A * 4/1982 Swinney .................. B44D 3/24 224/268
(Continued)

FOREIGN PATENT DOCUMENTS

DE 102019217937 A1 5/2021
EP 3701987 A1 9/2020
(Continued)

OTHER PUBLICATIONS

International Search Report, with English translation, issued in corresponding International Application No. PCT/EP2023/059209, date of mailing Jul. 12, 2023 (11 pages).
(Continued)

*Primary Examiner* — Vishal Pancholi
(74) *Attorney, Agent, or Firm* — FLYNN THIEL, P.C.

(57) ABSTRACT

A dispenser for pharmaceutical or cosmetic media, including a housing, a media reservoir and a discharge opening, wherein medium from the media reservoir is delivered into a surrounding atmosphere through the discharge opening. The dispenser has an electronic analysis unit for detecting usage of the dispenser, and the electronic analysis unit is configured for releasable attachment to the dispenser housing. The electronic analysis unit has a contact side which points in a direction of the housing in an attached state of the electronic analysis unit, and the electronic analysis unit has two parallel contact ribs on the contact side for bearing on the housing.

14 Claims, 6 Drawing Sheets

(51) Int. Cl.
*A61J 1/05* (2006.01)
*A61M 11/00* (2006.01)
*A61M 15/08* (2006.01)

(52) U.S. Cl.
CPC ....... *A61M 15/08* (2013.01); *A45D 2200/056* (2013.01); *A45D 2200/057* (2013.01); *A61M 2205/332* (2013.01); *A61M 2205/8206* (2013.01)

(58) Field of Classification Search
CPC .. A61M 2205/8206; A61M 2202/0468; A61M 2202/064; A61M 2205/3375; A61M 2205/3592; A61M 2205/505; A61M 2205/581; A61M 2205/582; A61M 2205/583; A61M 2205/6054; A61M 2209/00; A61M 15/0065; A61M 11/007; A45D 40/26; A45D 2200/056; A45D 2200/057; A61J 1/05; B05B 11/108; G16H 20/13; G16H 40/63
See application file for complete search history.

(56) References Cited

U.S. PATENT DOCUMENTS

| | | | | | |
|---|---|---|---|---|---|
| 5,020,527 | A * | 6/1991 | Dessertine | A61M 15/0065 | 128/200.14 |
| 5,105,958 | A * | 4/1992 | Patton | A63B 55/408 | 215/229 |
| 5,411,173 | A * | 5/1995 | Weinstein | G01F 11/006 | 128/200.22 |
| 5,741,275 | A | 4/1998 | Wyssmann | | |
| 5,809,997 | A * | 9/1998 | Wolf | A61M 15/0005 | 128/200.23 |
| 6,029,659 | A * | 2/2000 | O'Connor | A61M 15/009 | 128/200.23 |
| 6,059,245 | A * | 5/2000 | Hermansen | B62J 11/04 | 248/316.5 |
| 6,202,642 | B1 * | 3/2001 | McKinnon | A61M 15/0083 | 128/200.14 |
| 6,651,844 | B2 | 11/2003 | Tomaka et al. | | |
| 8,342,172 | B2 | 1/2013 | Levy et al. | | |
| 11,260,182 | B2 | 3/2022 | Udagawa et al. | | |
| 2013/0076514 | A1 | 3/2013 | Wegelin et al. | | |
| 2015/0024335 | A1 | 1/2015 | Sabourin | | |
| 2017/0246406 | A1 | 8/2017 | Sutherland | | |
| 2017/0323553 | A1 | 11/2017 | Engelhard et al. | | |
| 2019/0307648 | A1 | 10/2019 | Bartos | | |
| 2020/0288788 | A1 | 9/2020 | Vora et al. | | |
| 2020/0330719 | A1 | 10/2020 | Segal et al. | | |
| 2020/0345588 | A1 | 11/2020 | Merrell et al. | | |
| 2020/0405579 | A1 | 12/2020 | Shukla | | |
| 2021/0090703 | A1 | 3/2021 | Natarajan et al. | | |
| 2023/0129079 | A1 | 4/2023 | Karge et al. | | |
| 2024/0024157 | A1 | 1/2024 | Mercier | | |

FOREIGN PATENT DOCUMENTS

| | | | |
|---|---|---|---|
| EP | 4137184 | A1 | 2/2023 |
| EP | 4169500 | A1 | 4/2023 |
| KR | 101994297 | B1 | 6/2019 |
| WO | 9325841 | A1 | 12/1993 |
| WO | 2011056889 | A1 | 5/2011 |
| WO | 2014004437 | A1 | 1/2014 |
| WO | 2015193833 | A2 | 12/2015 |
| WO | 2017141194 | A1 | 8/2017 |
| WO | 2021175841 | A1 | 9/2021 |
| WO | 2021209320 | A1 | 10/2021 |

OTHER PUBLICATIONS

Written Opinion of International Searching Authority, issued in corresponding International Application No. PCT/EP2023/059209, date of mailing Jul. 12, 2023 (16 pages).

* cited by examiner

DISPENSER AND ANALYSIS UNIT FOR SAME

FIELD OF INVENTION

The invention relates to a dispenser for discharging pharmaceutical or cosmetic media, and in particular to an electronic analysis unit for such a dispenser.

BACKGROUND OF THE INVENTION

A dispenser of the generic type serves for discharging media, in particular pharmaceutical liquids. It is known to provide such dispensers with analysis units which detect the usage of the dispenser via a sensor system, for example in order to permit a subsequent check as to whether a medicament is taken correctly and in accordance with a medication plan.

Known analysis units are structurally integrated in the respective dispenser or are releasably attached to the dispenser, so that they can be detached from the dispenser and attached to another dispenser of the same type.

Due to many different types of dispensers, the respective complexity required to upgrade the dispensers with analysis units is considerable.

OBJECT AND ACHIEVEMENT

It is an object of the invention to provide an analysis unit for a dispenser, which allows the use with dispensers of different types and for the analysis unit to be reliably fastened to these different dispensers for the purpose of detecting the usage.

According to the invention, a dispenser for discharging pharmaceutical or cosmetic media, which has an electronic analysis unit, is proposed. The invention moreover relates to the analysis unit per se.

A dispenser according to an aspect of the invention has a housing which forms the outer contour of the dispenser and can be of a multi-part design. In particular, such a housing may have a reservoir body which forms the media reservoir and in particular a liquid reservoir in which the medium, in particular a pharmaceutical liquid, is stored before discharge.

The dispenser has a discharge opening through which medium from the media reservoir can be delivered into a surrounding atmosphere.

The dispenser is preferably designed for dispensing liquid, in particular in the form of a jet, a spray jet, or in the form of individual droplets. Alternatively, the dispenser may however also be provided for other media, for example, in particular for dispensing powder for the purpose of inhalation.

If the dispenser is designed as a liquid dispenser, the dispenser may in particular be a pump dispenser which has a manually activatable pump device which conveys liquid from the liquid reservoir to the discharge opening. Alternatively, the dispenser is a squeeze-bottle dispenser which has an elastically deformable reservoir body, liquid being able to be discharged by manually compressing the elastically deformable reservoir body.

The dispenser may furthermore be designed as an inhaler, in particular as a dispenser with a container which can be depressed for delivering a dose of the liquid, for the delivery of a defined dose of the medicament. According to a further example, the dispenser may be designed as a nasal dispenser, in particular with an elongate nasal applicator, at the distal end of which the discharge opening is provided.

The electronic analysis unit is designed for detecting the usage of the dispenser. For this purpose, the electronic analysis unit has electrical or electronic components, in particular a battery, a processor and at least one sensor. The sensor is used to capture data which allow conclusions to be drawn about the usage of the dispenser. The sensors can be designed to directly detect an external application of force, such as occurs for example when a hand-operated actuator for carrying out a pumping actuation is depressed. Preferably, however, at least one sensor which can detect data without contact and without external application of force is provided, it being possible for the sensor to be in particular a microphone and/or a movement sensor. These types of sensors are particularly suitable for use on dispensers of different types and types of application, without the need for a dispenser type-specific adjustment to the hardware. For example, the output data of a microphone may be evaluated in order to detect characteristic noises in the respective dispenser type during use.

The analysis unit preferably comprises an output device, in particular in the form of at least one LED, a display, a vibrator and/or a loudspeaker, in order to output signals to the user, for example in order to transmit the information that a discharge has been sensed or is pending according to the medication plan.

The analysis unit is preferably designed to be used together with an external device such as in particular a smartphone. For communication with the external device, the analysis unit preferably has a wireless module, in particular a Bluetooth and/or WIFI wireless module, or else a GSM/3G/4G or 5G wireless model.

The analysis unit is provided for releasable attachment to the housing of the dispenser, and in particular to the reservoir body of the housing. In order to enable secure bearing of the analysis unit on the housing, the electronic analysis unit has a contact side which in the attached state of the analysis unit points in the direction of the housing of the dispenser, wherein at least two mutually parallel contact ribs are provided on this contact side for bearing on the housing. The ribs are preferably precisely two or three mutually parallel contact ribs, while the individual contact ribs may also be interrupted and may consist of mutually aligned rib segments. The ribs form raised regions for bearing on the housing. The ribs preferably have a length of between 10 mm and 30 mm. The width of the ribs is preferably 5 mm or less, in particular preferably 3 mm or less. On a side of the ribs facing the housing, the ribs are preferably provided with a rounded edge.

The analysis unit is preferably provided for releasable attachment to a shell face of the reservoir body of the housing. The reservoir body preferably has a cylindrical shape in the region of the shell face, in particular with a circular or an elliptical cross section.

The analysis unit preferably has an electronics housing which forms the contact side, within which the electronic components of the analysis unit are arranged, that is to say in particular a processor, a memory and a battery and, depending on the type of evaluation, one or a plurality of sensors. The electronics housing does not completely surround the housing of the dispenser and in particular the reservoir body, but is preferably provided on one side of the reservoir body in the manner of a backpack, such that the dispenser, including the analysis unit, is thereby imparted an asymmetrical shape. In particular, the electronics housing preferably covers in the circumferential direction at most 50% of the shell face of the reservoir body, preferably at most 40%.

So that the electronics housing bearing in such a way on a side of the dispenser on the surface is held, preferably at least one fastening element which is attached to the electronics housing and by which the electronics housing is attached to the shell surface is provided. The fastening element or the fastening elements are in particular in the form of holding arms or in the form of a flexible fastening strap, as will yet be described hereunder.

The contact ribs, which in the assembled state bear on the dispenser housing as per the intended use, are preferably provided on a rear side of this electronics housing of the analysis unit. The contact ribs in terms of the circumferential direction of the reservoir body are preferably located in a sub-region of the shell surface of at most 40% of the circumference of the reservoir body, preferably in a sub-region of the shell surface of at most 25% of the circumference of the reservoir body.

The contact ribs preferably extend purely vertically, meaning the direction of main extent in terms of a cylindrical shape of the reservoir body.

A set-back intermediate region, which separates the contact ribs from one another, is provided between the at least two contact ribs. In this intermediate region, the contact side of the analysis unit is recessed in such a way that analysis unit does not bear on the housing of the dispenser. The contact between the contact side and the housing of the dispenser is accordingly restricted to the at least two contact ribs.

An analysis unit with such contact ribs allows reliable bearing on the housing of the dispenser, since the contact pressure force acts in defined bearing regions. Moreover, the contact ribs allow bearing on housings of different dimensions and, in particular, reservoir bodies with differently curved outer contours.

The contact ribs lead to a firm hold of the analysis unit on the housing of the dispenser and in particular on the reservoir body. As intended, the contact ribs remain stationary relative to the shell face of the reservoir body when the analysis unit is attached. Relative mobility during operation is not desired.

The radii of curvature of such outer contours are covered in each case depends on the geometry of the contact side. Preference is given to a design in which the contact ribs are at mutual spacing of at least 8 mm, wherein the contact ribs preferably rise up by at least 1 mm, preferably by at least 1.5 mm, above the bearing surface in the intermediate region. Two contact ribs between which an intermediate region of 8 mm that is recessed 1 mm is provided may be attached to housing sections with a radius of curvature greater than 10 mm without the housing section coming into contact with the contact side away from the contact ribs. With an intermediate region of 8 mm in width that is recessed by 1.5 mm, attachment up to a radius of curvature of approximately 6 mm is possible.

The contact ribs preferably have a spacing of at most 20 mm, or in comparison to the diameter of the reservoir body a relatively smaller spacing, in particular a spacing which is at most 80% of the diameter of the reservoir body.

One or a plurality of the contact ribs can be attached to an elastic cantilever, in particular to a cantilever in the form of a plastic tongue which is cut free on three sides and allows a resilient behavior orthogonal to the contact side. It can also be provided that one or a plurality, but not all, of the contact ribs are deflectable in such a manner, while at least one contact rib is provided as fixed and non-deflectable on the contact side of the analysis unit. One possible setup provides for example three contact ribs, of which one or two are in each case attached to an elastic cantilever, while the third contact rib is provided as stationary on the contact side. A rib design with two contact ribs which are both deflectable may also be expedient.

In the case of a contact rib, which consists of a plurality of mutually aligned rib segments, it can be advantageous when these rib segments are provided on separate elastic cantilevers.

The contact ribs are not sufficient to attach the analysis unit to the housing of the dispenser, but merely ensure that the analysis unit bears securely on the outside of the housing.

Various concepts are possible for the purpose of fastening thereto.

In a preferred type of design, it is provided that the electronic analysis unit has a dimensionally flexible fastening strap which is attached to the analysis unit and surrounds the housing, in particular the reservoir body. The analysis unit is pressed against the housing by the fastening strap. Conjointly with the contact ribs, a secure hold can be achieved.

The fastening strap can be designed as an elastic strap or as a largely inelastic strap. In particular when using an inelastic strap, it is expedient to provide at least one contact rib on an elastically deflectable cantilever.

If the fastening strap is elastic, the strap can be used without length adjustment for housings and especially reservoir bodies of different sizes.

Preferably, the fastening strap is formed from a material other than that of the electronics housing and produced as a separate element, and subsequently attached to the electronics housing.

The fastening strap can be fastened to the electronics housing of the analysis unit in various ways. A preferred design provides that the fastening strap is closed in an encircling manner and is placed in two strands around the housing, wherein the two respective end-side loops are or will be attached to the housing. Fastening to the housing of the analysis unit is easy due to the loops. A fastening strap which is placed in such a two-stranded manner around the housing of the dispenser preferably has a circular cross section and can be formed by a simple O-ring.

It is also possible to design the fastening strap as a closed strap which completely surrounds the housing of the dispenser. In such a design, the strap can be arranged in particular in a circumferentially closed and continuous chamber of the housing of the analysis unit, and thus be securely fastened to the analysis unit.

In particular, in a slightly elastic strap, it can be expedient that the fastening strap comprises two strap portions which are each attached to a main unit or a housing of the analysis unit. The two strap portions are connectable to one another in the region of a closure such as a magnetic or hook-and-loop closure, so as to thereby secure the analysis unit to the housing of the dispenser. The fastening strap can also be designed as a variable-length strap, which can be established in a desired length configuration by a closure. It can be expedient when the closure has interacting closure elements on both strap portions, wherein a plurality of closure elements are preferably provided on one of the strap portions, so that, depending on the circumference of the housing, a suitable closure element can in each case be selected for joining the strap portions.

Alternatively or additionally to the strap, a magnetic or magnetizable holding surface can also be provided on the outside of the housing of the dispenser, in particular on the reservoir body. This allows the analysis unit to be placed in the region of this holding surface, wherein for this purpose the contact side of the analysis unit is designed to be magnetic or magnetizable in order to correspond to the housing-proximal holding surface.

Preferably, a magnetizable, and in particular a metallic, holding surface is provided on the housing, while at least one permanent magnet is provided on the analysis unit, though the reverse setup is also possible. A design in which the holding surface as well as the magnetic design of the analysis unit is implemented using permanent magnets is also possible.

In particular, neodymium magnets come into consideration as permanent magnets, since such magnets provide a strong magnetic force and are therefore particularly advantageous for the secure fastening of the analysis unit on the housing of the dispenser.

The holding surface provided on the housing can be provided in various ways. It is particularly preferred if the holding surface is provided in the region of an inscribed label. It may directly form the label or be adhesively bonded to a housing surface of the housing by means of the label. The holding surface may also be self-attached independently of the label to the housing by means of an adhesive connection. Designs in which the holding surface is formed by a holding sleeve or holding clamp which is attached to the housing of the dispenser in a clamping manner are also possible.

Another possibility of fastening the analysis unit to the housing provides that the analysis unit has at least two, and preferably at least three, elastically deflectable holding arms which encompass the housing, in particular a reservoir body of the housing, and thus cause a clamping hold between the analysis unit and the housing. Preferably, at least three holding arms are provided, of which two holding arms extend in a first direction of extent and of which the third holding arm is arranged between these two holding arms and extends in the opposite direction of extent.

The analysis unit can have a housing that is of a non-modular construction and cannot be further disassembled by the user. However, a particular embodiment of a dispenser according to an embodiment of the invention and of an analysis unit according to an embodiment of the invention provides that the analysis unit comprises a fastening unit and an electronics unit that represent separate structural units.

The fastening unit is designed for releasable attachment to the housing and forms the contact side of the analysis unit and the contact ribs provided on the latter. The electronics unit which can be disconnected therefrom is provided for releasable attachment to the fastening unit. The electronics unit preferably comprises the entirety of the electronic components of the analysis unit, but at least the battery, the processor and at least one sensor.

The division of the analysis unit into two parts allows the electronics unit to be used with different fastening units of which not all must have contact ribs in the manner described above. However, different fastening units may also be provided, each having contact ribs, wherein these are differently designed and in particular spaced apart so that the fastening units are each suitable for dispenser housings of different shapes.

The same electronics unit can accordingly be provided by a configuration with different fastening units for attachment to many different dispensers.

The possibility of separating the fastening unit and the electronics unit and reassembling them in another configuration does not mandatorily have to be provided for the end user. The modularity can also be used to provide uniform electronics units with matching fastening units in accordance with requirements, and possibly fixedly connect the electronics units with the matching fastening units, already in the course of production and provision.

It is particularly preferred, however, when the fastening unit is designed for attachment to the electronics unit such that the fastening unit can be released without tools, and thus the possibility of changing the fastening unit is available to the end user himself/herself. In particular, it can be provided for this purpose that the electronics unit is magnetically fastened on the fastening unit, or the electronics unit is fastened on the fastening unit by a latching mechanism having an elastically deflectable latching lug.

The fastening unit is preferably free from electronic components. However, the fastening unit can also be a carrier of sensors and/or have an electronically readable identification feature, for example an identification feature which is stored in an RFID chip of the fastening unit and can be read by a sensor of the electronics unit. As a result, it is possible to record to which fastening unit the electronics unit is connected.

The analysis unit according to an embodiment of the invention the invention can be marketed conjointly with the dispenser, as a set. The analysis unit can however also be purchased separately, to use with existing dispensers. It can therefore be advantageous when the electronic analysis unit comprises a plurality of fastening straps which can be optionally attached to the analysis unit, in particular to the fastening unit. It is also possible that the analysis unit has a plurality of fastening units which can be optionally attached to the electronics unit, in order to configure the analysis unit for attachment to a specific type of dispenser.

BRIEF DESCRIPTION OF THE DRAWINGS

Further advantages and aspects of the invention will emerge from the claims and from the following description of preferred exemplary embodiments of the invention, which are explained below with reference to the figures in which:

DETAILED DESCRIPTION OF THE EXEMPLARY EMBODIMENTS

Figure 1:
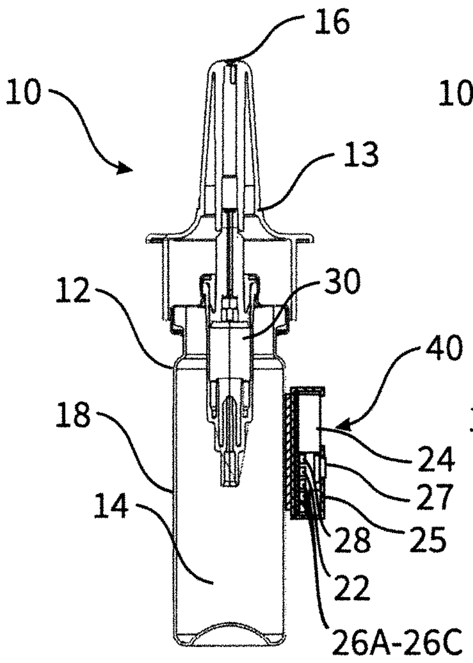
FIGS. 1 to 3 show, by way of example, a liquid dispenser according to an embodiment of the invention having an analysis unit according to an embodiment of the invention.
Figure 2:
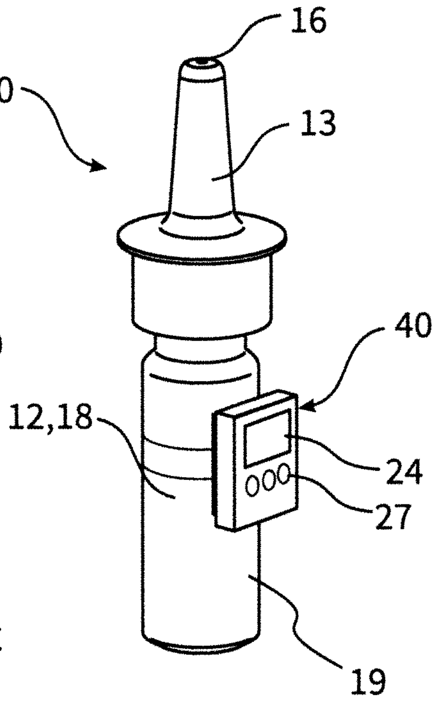
Figure 3:
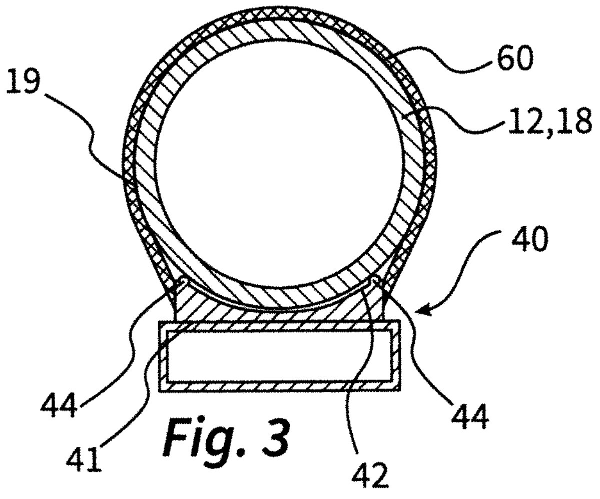

FIGS. 1 and 3 show a dispenser 10 according to an embodiment of the invention, which is designed for discharging pharmaceutical liquids. The liquid dispenser 10 is designed by way of example as a nasal dispenser and has an applicator part with an elongate nasal applicator 13, at the distal end of which a discharge opening 16 is provided. However, the specific type of dispenser should be understood as just an example. Embodiments of the invention likewise also comprises other dispensers for media and in particular liquids, in particular pharmaceutical dispensers, which are designed for the oral or topical delivery of medicaments.

By depressing the applicator part relative to a liquid reservoir 14 or the reservoir body 18 forming the liquid reservoir, it is possible to activate a pump device 30 which conveys liquid from the liquid reservoir 14 to the discharge opening 16.

In the case of a dispenser 10 according to an embodiment of the invention, it is provided that use of the dispenser 10 by the user is electronically detected. An electronic analysis unit 40 is provided for this purpose. In the present example, the electronic analysis unit 40 comprises a battery 25, a display device 24, a circuit board with a processor 28, operating elements 27 and various sensors 26A to 26C.

The sensors 26A-26C can comprise in particular a movement sensor which detects the orientation of the dispenser and/or accelerations. Furthermore, the sensors 26A-26C may comprise a microphone which detects noises that occur during the handling of the dispenser 10. The captured data are evaluated either directly by the processor 28, or entirely or partially on an external system which is connected to the analysis unit 40 via a wireless interface.

By way of example, the processor 28 may be designed to activate the microphone in the case of movements of the dispenser 10 detected by the movement sensor. Noises, in particular noises transmitted through the dispenser housing 12, can be detected by the microphone. In particular, the different phases of a pumping process, that is to say the dispensing of liquid from a pumping chamber and the renewed aspiration of liquid from the media reservoir 14 into the pumping chamber, are accompanied by characteristic noises which are readily distinguishable from one another.

The analysis unit 40 is attached to the reservoir body 18 of the dispenser housing 12, specifically to the shell face 19 of the substantially cylindrical reservoir body 18, presently a circular cylindrical reservoir body.

The analysis unit 40 does not surround the reservoir body 18, but is provided in the manner of a backpack on one side, such that the analysis unit 40 imparts to the dispenser an asymmetrical overall shape. The analysis unit, or the electronics housing 41 forming the main constituent part, span only a comparatively small part of the shell face in the circumferential direction, in the present case approximately 90° or a quarter of the circumference.

The analysis unit 40 has a fastening strap 60 which surrounds the reservoir body 18 and by which the analysis unit 40 is pressed to the reservoir body. The fastening strap is attached with both ends to the electronics housing 41 of the analysis unit.

In the process, the analysis unit 40, or more precisely the electronics housing 41, is not attached to the reservoir body 18 over the entire area, but in the region of contact ribs 44 which are provided on the contact side 42 of the analysis unit 40 on the rear of the electronics housing 41. In FIG. 3, this is illustrated by way of an example of a sectional representation.

The direct contact between the dispenser housing 12 and the analysis unit 44 is limited to the contact surfaces of the contact ribs 44 by the contact ribs 44, so that a comparatively large surface pressure and a secure hold is achieved here. In particular, the evaluation of sound waves, which are caused by the usage of the dispenser and are detected by the microphone in the intended use, is possible in a better way due to the contact ribs 44.

Figure 4:
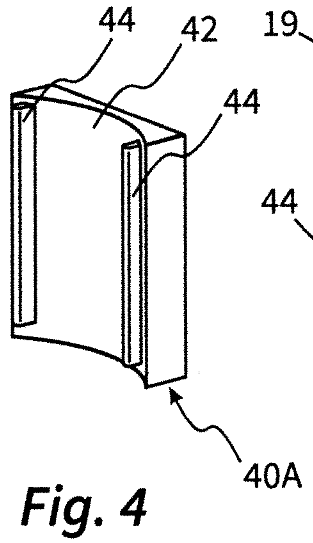
FIGS. 4 to 6 highlight a first configuration of contact ribs on a contact side of the analysis unit.
Figure 5:
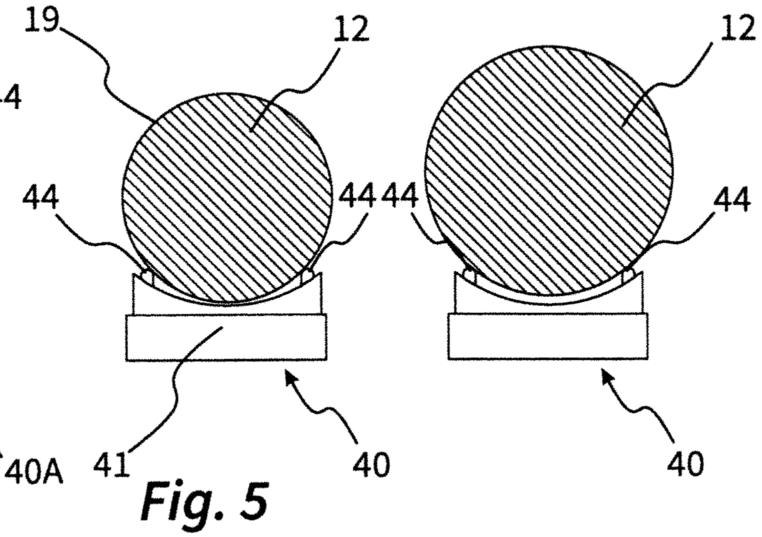
Figure 6:
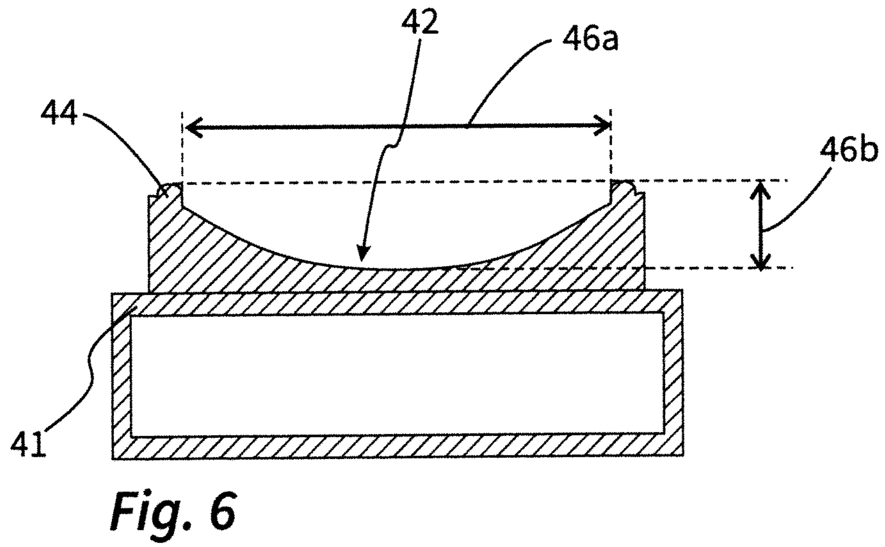

FIGS. 4 to 6 show a first configuration of contact ribs 44. The rear side of the analysis unit 40 is illustrated in FIG. 4. This rear side forms a contact side 42, wherein two mutually parallel contact ribs 44 are provided as stationary on the contact side 42. A recessed intermediate region is provided between the two contact ribs 44. As can be seen in FIG. 5, the contact ribs 44 make it possible to bear on dispenser housings 12 of different radii of curvature. The same analysis unit 40, or the same fastening unit 40A of the analysis unit 40, can therefore be used equally well for different dispensers 10.

FIG. 6 once again highlights the geometry of the contact side 42. It can be seen that the contact side 42 has a basically curved concave shape and that the two contact ribs 44 rise up above the curved concave shape. The spacing 46A corresponds to the width of the intermediate region. The spacing 46B indicates the extent to which the intermediate region is recessed at most relative to the contact ribs 44.

Figure 7:
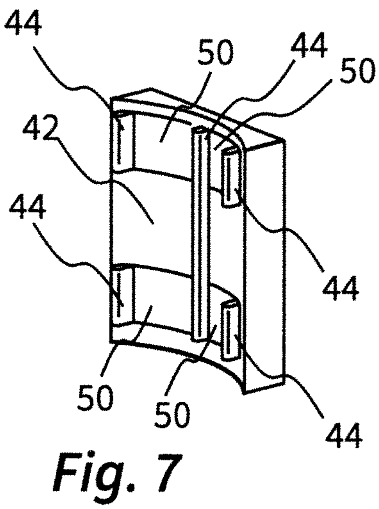
FIGS. 7 to 9 illustrate a second configuration of contact ribs on a contact side of the analysis unit.
Figure 8:
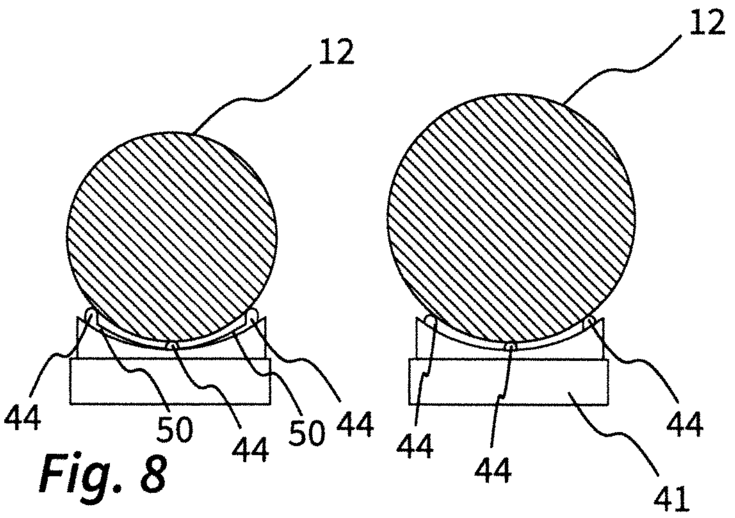
Figure 9:
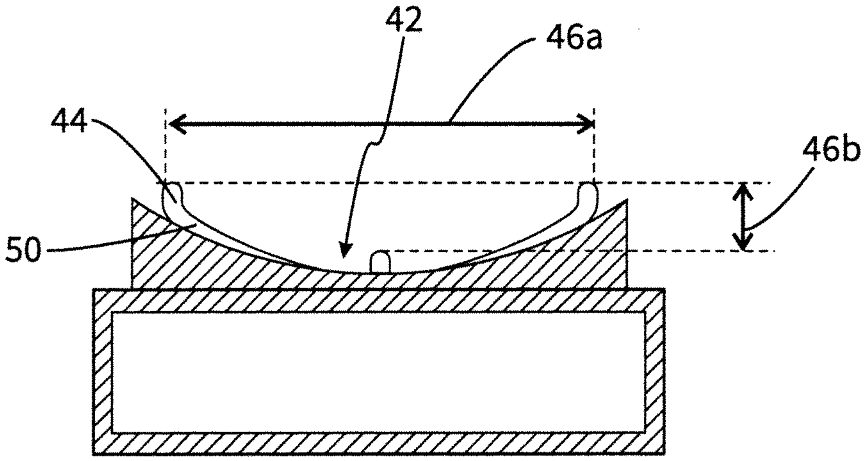

FIGS. 7 to 9 show a second configuration of contact ribs 44. As can be seen on the basis of FIG. 7, the contact side 42 is provided here with altogether three contact ribs 44. A central contact rib 44 is fixedly connected to the housing of the analysis unit 40 and cannot be deflected to a relevant extent relative to the latter. By contrast, two lateral contact ribs 44 are provided from cantilevers 50, wherein both lateral contact ribs 44 each consists of two mutually aligned rib segments, which in turn are in each case provided on a cantilever 50. The two outer contact ribs can therefore be resiliently deflected, whereby ribs move relative to the electronics housing 41.

The cantilevers 50 allow the outer contact ribs 44 to be displaced relative to one another counter to the spring force of the cantilevers 50. As a result, although there are altogether three contact ribs, all of the contact ribs bear in each case against the dispenser housing 12 when the analysis unit 40 is used with different dispenser housings 12 or reservoir bodies 18. In the case of dispenser housings 12/reservoir bodies 18 with larger diameters, the cantilevers 50 are elastically deflected, whereby this can be advantageous in particular in the context of a fastening of the analysis unit 40 with a fastening strap 60.

FIGS. 10 to 14 show different configurations of such a fastening strap 60. The respective fastening straps 60 illustrated are attached to a housing of the analysis unit 40 and are placed about the dispenser housing 12.

Figure 10:
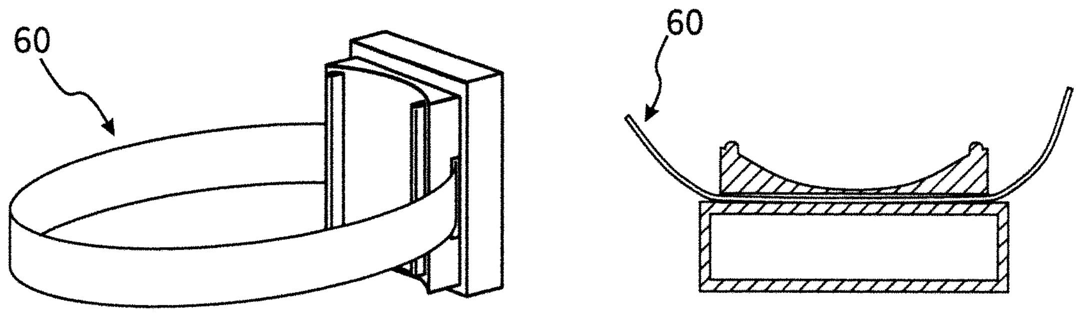
FIGS. 10 to 14 show different configurations of fastening straps for attaching the analysis unit to the housing of the dispenser.

In the design of FIG. 10, the fastening strap 60 is designed as a fully encircling fastening strap 60 which is guided in the area of the housing of the analysis unit 40 through a chamber 64 between an electronics unit 40B and the fastening unit 40A. The fastening strap is elastic and can be made of rubber, for example. The fastening strap allows the attachment to dispenser housings of different sizes.

Figure 11:
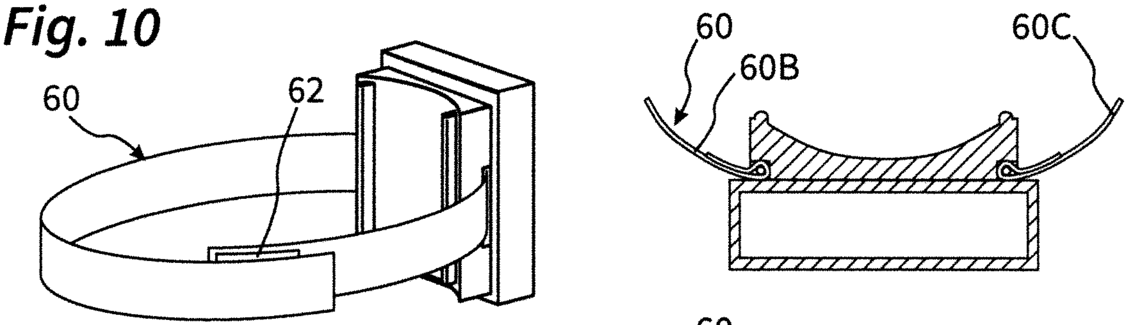

In the design according to FIG. 11, the fastening strap has two strap portions 60B, 60C, which are each attached to the housing of the analysis unit 40. The strap portions 60B, 60C can be placed around the dispenser housing 12 from both sides and connected to one another by means of a closure 62. For example, the closure 62 can be a magnetic closure.

Figure 12:
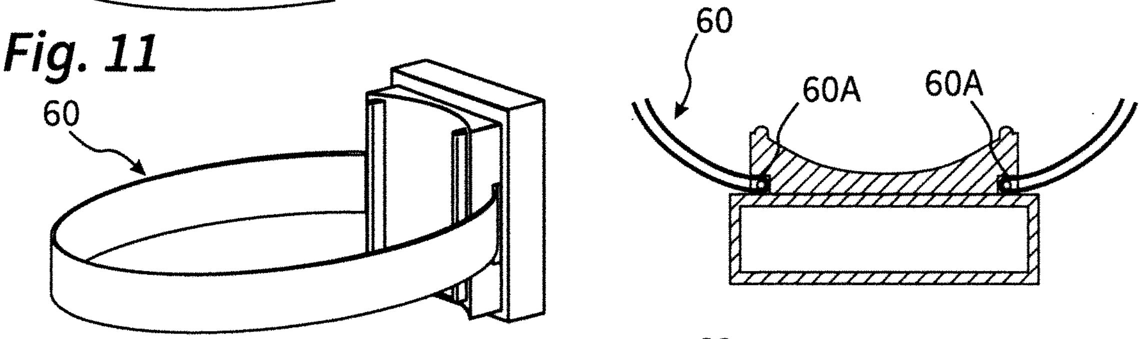

In the design of FIG. 12, a closed fastening strap 60 is used, which is however placed twice around the dispenser housing 12 and is placed in the form of two loops 60A in the area of the housing of the analysis unit, the two loops 60A being attached to the housing of the analysis unit 40.

Figure 13:
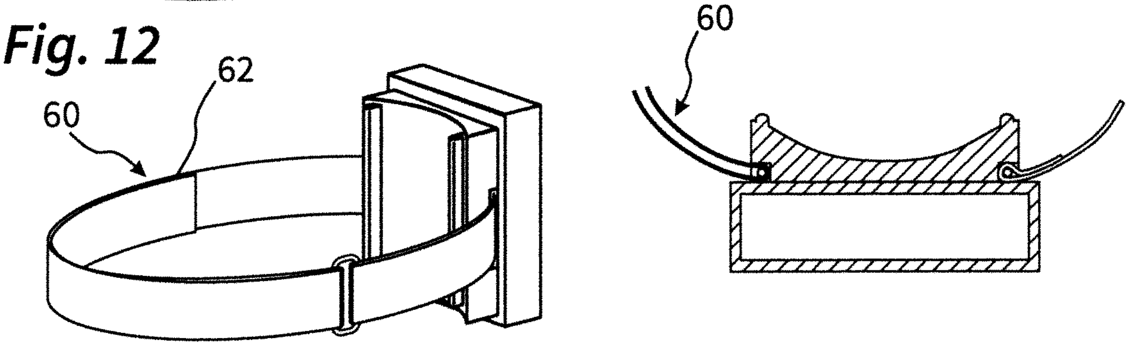

The design of FIG. 13 provides that the fastening strap 60 used there is of a variable-length design and can be secured in the correct setting for the dispenser housing by means of a closure 62.

Figure 14:
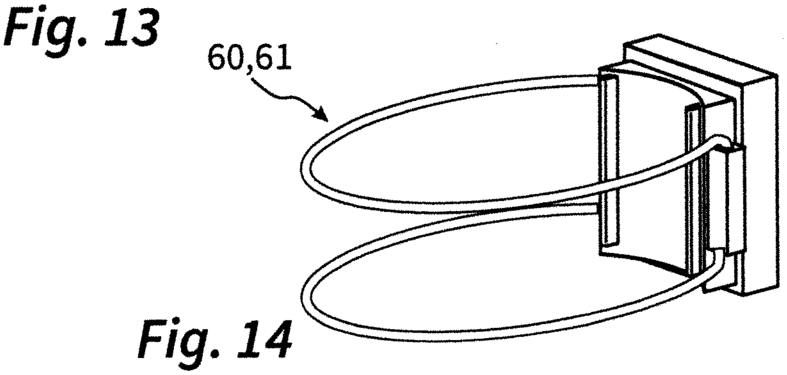

The design of FIG. 14 is similar to that of FIG. 12. Here, too, a closed fastening strap 60 is used, which is placed around the dispenser housing 12 in two strands and which forms two loops in the region of the ends thereof, which are attached to the housing of the analysis unit 40. Deviating from the design of FIG. 12, in which a flat fastening strap 60 is used, the fastening strap 60 of FIG. 14 is formed as an O-ring with a circular cross section.

Figure 15:
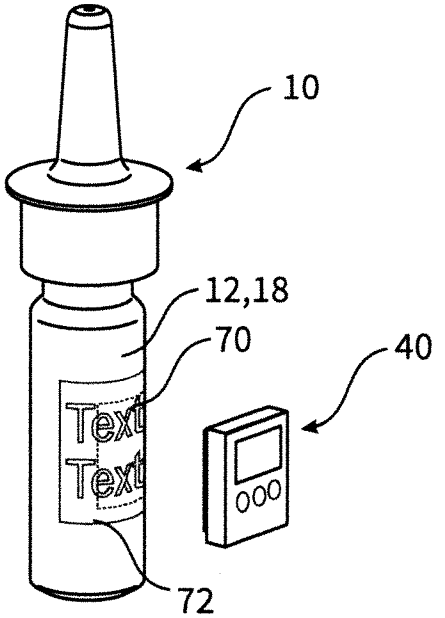
FIGS. 15 to 17 show the magnetic attachment of the analysis unit to the housing of the dispenser.
Figure 16:
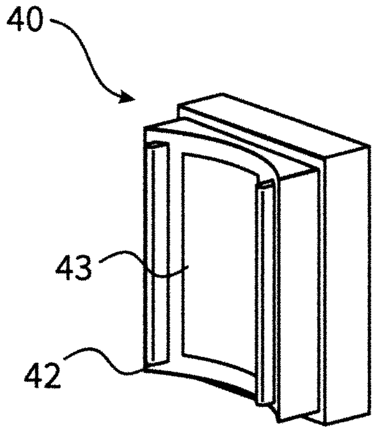
Figure 17:
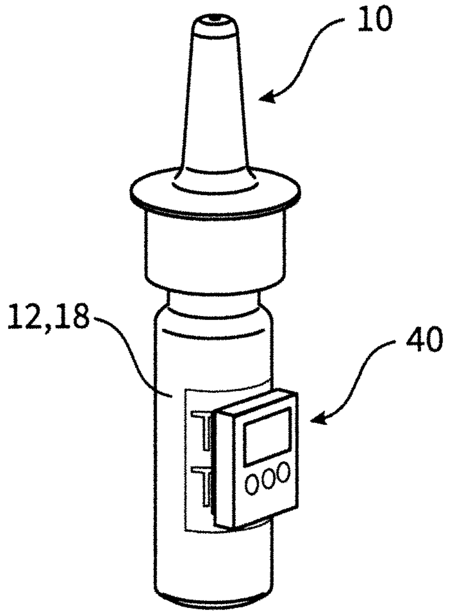

FIGS. 15 to 17 show another form of fastening an analysis unit 40 to the dispenser housing 12. A label 72 is attached to the reservoir body 18 of the dispenser 10. In the label 72, a magnetizable holding surface 70 is integrated, which consists, for example, of a magnetizable metal.

Correspondingly, a permanent magnet 43 is provided on the contact side 42 of the analysis unit 40. If the analysis unit 40 is guided into the region of the holding surface 70, the analysis unit 40 is magnetically attracted and thus magnetically connected to the reservoir body 18, as shown in FIG. 17. The permanent magnet 43 is preferably designed as a neodymium magnet in order to cause a holding force sufficient for a secure hold.

Figure 18:
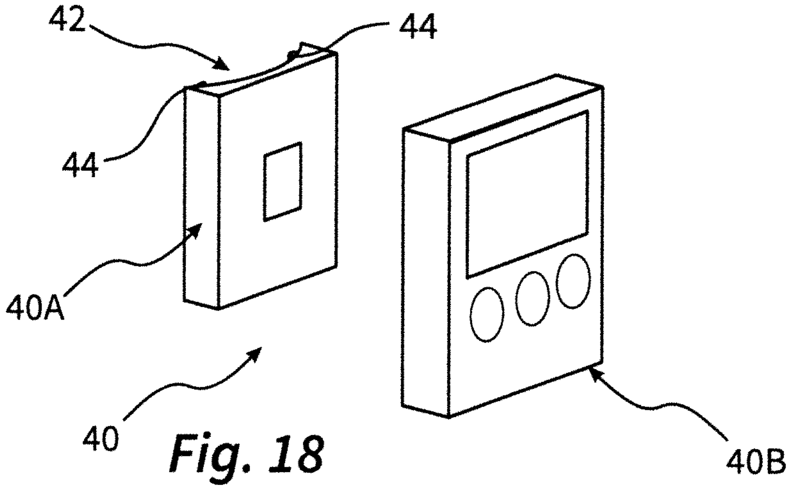
FIGS. 18 to 21 show a potential modular embodiment of the analysis unit with a fastening unit and an electronics unit, and also a coupler for coupling the electronics unit to the fastening unit.
Figure 19:
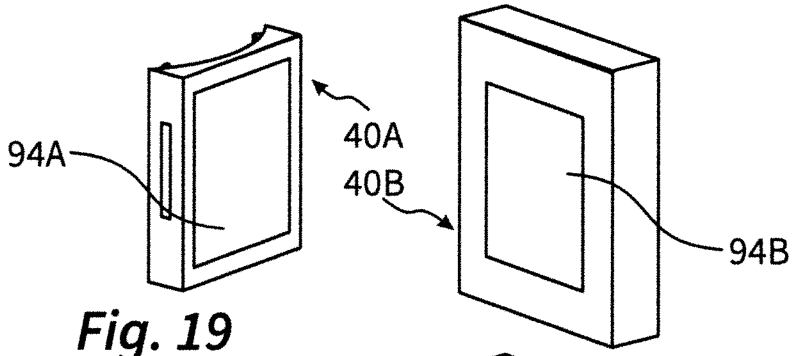

FIGS. 18 to 21 highlight the possibility of designing the analysis unit 40 in a modular manner. As is illustrated in FIG. 18, in such cases the analysis unit 40 is subdivided into a fastening unit 40A on which the contact side 42 as well as the contact ribs 44 are provided, and an electronics unit 40B which has the predominant number of electrical/electronic components, preferably the entirety of the electronic components. It can however be provided that the fastening unit 40A has an electronic identification means such as an RFID chip in order that the electronics unit 40B can detect whether the electronics unit 40B is connected to a fastening unit 40A, or to which fastening unit 40A it is connected.

The subunits 40A, 40B can preferably be coupled to one another without tools. In the case of the design of FIG. 19, the two subunits are connected to magnetic or magnetizable coupling surfaces 94A, 94B.

Figure 20:
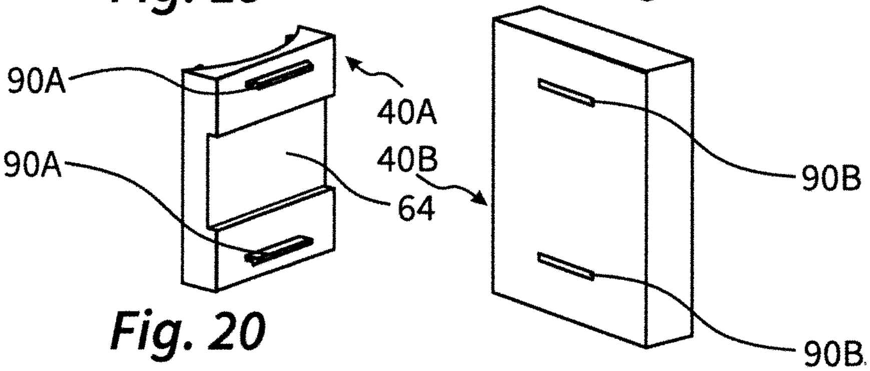

In the case of the design of FIG. 20, latching lugs 90A which latch into latching openings 90B on the electronics unit 40B are provided on the fastening unit 40A. Preferably, as a difference from the design of FIG. 20, the latching lugs 90A can be deflected manually in order to be able to separate the connection again. It can however also be provided that the connection of the electronics unit 40B to the fastening unit 40A according to the intended use is non-releasable, such that a corresponding coupling is possible only once, in particular in the case of fixing onto a specific fastening unit 40A that already takes place in the course of production. In the design of FIG. 20 it is also evident that a depression is provided on one of the units, presently on the fastening unit 40A, which serves to form the chamber 64 and to receive a fastening strap 60.

Figure 21:
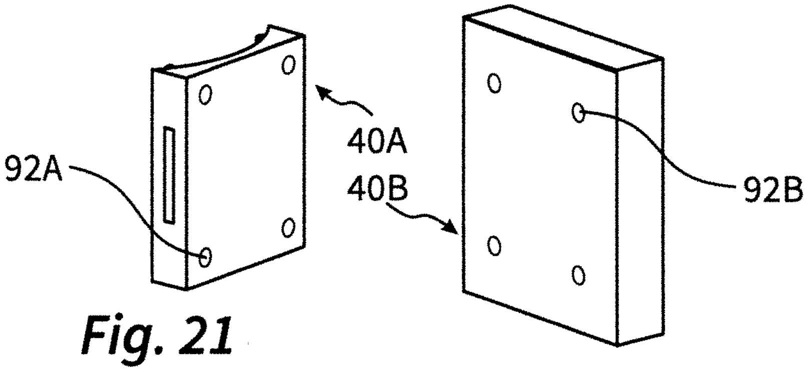

In the case of the design of FIG. 21, screw holes 92A, 92B are provided on the electronics unit 40B and the fastening unit 40A, through which the two subunits can be screwed to one another. This type of connection is usually not intended to be released by the end user, but serves the purpose of being able to connect a standard electronics unit 40B permanently to a fastening unit 40A in the course of production.

The invention claimed is:

1. A dispenser for discharging pharmaceutical or cosmetic media, comprising:

a housing including a reservoir body;

a media reservoir in the reservoir body;

a discharge opening, wherein medium from the media reservoir is deliverable into a surrounding atmosphere through the discharge opening; and an electronic analysis unit for detecting usage of the dispenser, the electronic analysis unit being configured for releasable attachment to the housing of the dispenser, the electronic analysis unit comprising:

a contact side, the contact side in an attached state of the electronic analysis unit to the dispenser pointing in a direction of the housing;

two mutually parallel contact ribs disposed on the contact side and bearing on the housing, the contact ribs having a mutual spacing smaller than a diameter of the reservoir body and not more than 80% of the diameter of the reservoir body; and a flexible fastening strap surrounding the reservoir body.

2. The dispenser as claimed in claim 1, wherein the reservoir body has a shell face, the electronic analysis unit is configured for releasable attachment to the shell face of the reservoir body, the shell face being a circular-cylindrical shell face, the electronic analysis unit has an electronics housing and electronic components, the electronic components being arranged in the electronics housing, the contact ribs being disposed on the contact side and comprising vertically extending contact ribs, and the electronics housing covers in a circumferential direction at most 50% of the shell face of the reservoir body.

3. The dispenser as claimed in claim 2, wherein the contact ribs remain stationary relative to the shell face of the reservoir body when the dispenser is operated.

4. The dispenser as claimed in claim 1, wherein the reservoir body has a shell face, the electronic analysis unit is configured for releasable attachment to the shell face, the shell face being a circular-cylindrical shell face, and the contact ribs, in terms of a circumferential direction of the reservoir body, are located in a sub-region of the shell face of at most 40% of a circumference of the reservoir body.

5. The dispenser as claimed in claim 1, wherein the dispenser includes at least one of the following:

the contact ribs have a mutual spacing of at least 8 mm;

the contact ribs have a mutual spacing of at most 20 mm; and the contact ribs project outwardly by a spacing of at least 1.5 mm in relation to an intermediate region lying between the contact ribs.

6. The dispenser as claimed in claim 1, wherein at least one of the contact ribs is attached to an elastic cantilever.

7. The dispenser as claimed in claim 1, wherein the contact ribs comprise a plurality of mutually aligned rib segments each provided on an elastic cantilever.

8. The dispenser as claimed in claim 1, wherein the electronic analysis unit comprises an electronics housing, and the fastening strap comprises a separate element and is of a material different from a material of the electronics housing.

9. The dispenser as claimed in claim 8, wherein:

the fastening strap is configured as an elastic strap, and the fastening strap comprises at least one of the following:

an O-ring;

a closed strap comprising a double strap surrounding the housing and being fastened in a region of two deflecting loops to a main unit of the electronic analysis unit; and a closed strap attached to the housing to completely surround the housing.

10. The dispenser as claimed in claim 1, wherein:

the fastening strap comprises two strap portions each fastened to a main unit of the electronic analysis unit and connected to each other in a region of a closure; or the fastening strap is configured as a variable-length strap, the variable-length strap being adjustable to a desired length configuration by a closure.

11. The dispenser as claimed in claim 1, further including at least one of the following:

the electronic analysis unit comprises at least one sensor comprising a movement sensor and/or a microphone;

the electronic analysis unit comprises an output device comprising at least one LED, a display device, a vibrator and/or a loudspeaker; and the electronic analysis unit comprises a wireless module comprising a Bluetooth and/or WIFI wireless module; and/or the electronic analysis unit comprises an energy source comprising a battery.

12. The dispenser as claimed in claim 1, wherein the dispenser includes one of the following:

the dispenser is configured as a squeeze-bottle dispenser and the media reservoir comprises an elastically deformable reservoir body, wherein liquid is discharged by manually compressing said elastically deformable reservoir body;

the dispenser is configured as a pump dispenser having a manually activatable pump device to convey the liquid from the media reservoir to the discharge opening;

the dispenser is configured as a spray dispenser;

the dispenser is configured as an inhaler having a depressible container for delivering a dose of liquid;

the dispenser is configured as a drop dispenser having a drop-formation surface surrounding the discharge opening; or the dispenser is configured as a nasal dispenser with an elongate nasal applicator having a distal end, the discharge opening being located at the distal end;

the media reservoir has a volume of up to 200 ml; and the media reservoir is filled with a pharmaceutical liquid.

13. An electronic analysis unit for a dispenser for discharging pharmaceutical or cosmetic media and having a housing, the electronic analysis unit being releasably attachable to the dispenser and comprising:

at least one sensor for detecting usage of the dispenser;

a contact side, the contact side, in an attached state of the electronic analysis unit to the dispenser, pointing in a direction of the housing of the dispenser; and two mutually parallel contact ribs for bearing on the housing of the dispenser, the two contact ribs being disposed on the contact side, the contact ribs having a mutual spacing smaller than a diameter of a reservoir body of the dispenser when connected to the dispenser and not more than 80% of the diameter of the reservoir body of the dispenser when connected to the dispenser; and a flexible fastening strap for surrounding the reservoir body of the dispenser when connected to the dispenser.

14. The dispenser as claimed in claim 10, further including at least one of the following:

the closure is configured as a hook-and-loop fastener;

the closure has interacting closure elements on both strap portions, and a plurality of closure elements are disposed on one of the strap portions; and the closure is configured as a magnetic closure.

* * * * *